(12) United States Patent
Bortlik et al.

(10) Patent No.: US 9,265,276 B2
(45) Date of Patent: Feb. 23, 2016

(54) REDUCING ASTRINGENCY IN COMPOSITIONS CONTAINING PHENOLIC COMPOUNDS

(75) Inventors: Karlheinz Bortlik, Syens (CH); Maurizio Beggio, Lausanne (CH); Pierre Lambelet, Saint-legier (CH); Tuong Huynh-Ba, Pully (CH); Robert Aeschbach, Vevey (CH)

(73) Assignee: Nestec S.A., Vevey (CH)

( * ) Notice: Subject to any disclaimer, the term of this patent is extended or adjusted under 35 U.S.C. 154(b) by 64 days.

(21) Appl. No.: 13/121,107

(22) PCT Filed: Sep. 14, 2009

(86) PCT No.: PCT/EP2009/061891
§ 371 (c)(1),
(2), (4) Date: Jun. 9, 2011

(87) PCT Pub. No.: WO2010/034642
PCT Pub. Date: Apr. 1, 2010

(65) Prior Publication Data
US 2011/0269851 A1    Nov. 3, 2011

(30) Foreign Application Priority Data
Sep. 25, 2008  (EP) ..................................... 08105432

(51) Int. Cl.
| | |
|---|---|
| *A61K 41/00* | (2006.01) |
| *A23L 1/22* | (2006.01) |
| *A23F 3/40* | (2006.01) |
| *A23L 1/03* | (2006.01) |
| *A23L 1/30* | (2006.01) |
| *A23L 2/52* | (2006.01) |

(52) U.S. Cl.
CPC ............... *A23L 1/22075* (2013.01); *A23F 3/40* (2013.01); *A23L 1/033* (2013.01); *A23L 1/3002* (2013.01); *A23L 2/52* (2013.01); *A23V 2002/00* (2013.01)

(58) Field of Classification Search
USPC ....................................................... 514/784
See application file for complete search history.

(56) References Cited

U.S. PATENT DOCUMENTS

| 4,906,480 | A | * | 3/1990 | Kashket ........................... 426/3 |
| 5,527,552 | A | * | 6/1996 | Todd, Jr. ........................ 426/541 |
| 6,291,533 | B1 | * | 9/2001 | Fleischner .................... 514/682 |
| 2005/0129829 | A1 | * | 6/2005 | Hosoya et al. .................. 426/597 |
| 2005/0220857 | A1 | | 10/2005 | Purpura et al. |
| 2008/0213441 | A1 | * | 9/2008 | Ludwig et al. ................ 426/310 |

FOREIGN PATENT DOCUMENTS

| JP | H089897 | 1/1996 |
| JP | H08332050 | 12/1996 |
| JP | 10150929 | 6/1998 |
| JP | H11240840 | 9/1999 |
| JP | 2001316259 | 11/2001 |
| JP | 2004073196 | 3/2004 |
| JP | 2005124540 | 5/2005 |
| RU | 2267276 | 1/2006 |
| WO | 2007039262 | 4/2007 |
| WO | 2007101675 | 9/2007 |
| WO | WO2008036234 | 3/2008 |
| WO | 2008083152 | 7/2008 |

OTHER PUBLICATIONS

Phosphatidylcholine' in http://lipidlibrary.aocs.org/lipids/pc/index.htm (retrieved from the internet Apr. 13, 2013).*
Machine Translation of JP 10-150929 A (1998).*
CAS Abstract of JP 10150929 (1998).*
Okubo "DMF (Dry Mouth Feel, Undesirable) Components of Soybean and Behavior of the Components on Soybean Food Processing" Nippon Shokuhia Kogyo Gakkaishi, vol. 35, No. 12, 1988, pp. 866-874.
International Search Report for PCT/EP2009/061891 date mailed Dec. 29, 2009, 4 pages.
European Patent Office Communication dated Apr. 12, 2011—Applicant Nestec S.A. EP Patent Application EP 08105432 (English Translation).
European Patent Office Communication dated Apr. 12, 2011—Applicant Nestec S.A. EP Patent Application EP 08105432.
Gibbs et al., "Encapsulation in the food industry: a review," International Journal of Food Sciences and Nutrition (1999) vol. 50, pp. 213-224.
Weiner, "Phospholipid :iposomes: Properties and Potential Use in Flavor Encapsulation," Chaper 16, (1995).

* cited by examiner

*Primary Examiner* — James O Wilson
*Assistant Examiner* — Oluwafemi Masha
(74) *Attorney, Agent, or Firm* — K&L Gates LLP

(57) ABSTRACT

The present invention in general relates to the field of taste. In particular it relates to the reduction of astringency. One embodiment of the present invention relates to the use of at least one phospholipid for the preparation of a phenol containing composition to reduce the astringency of the composition.

8 Claims, 1 Drawing Sheet

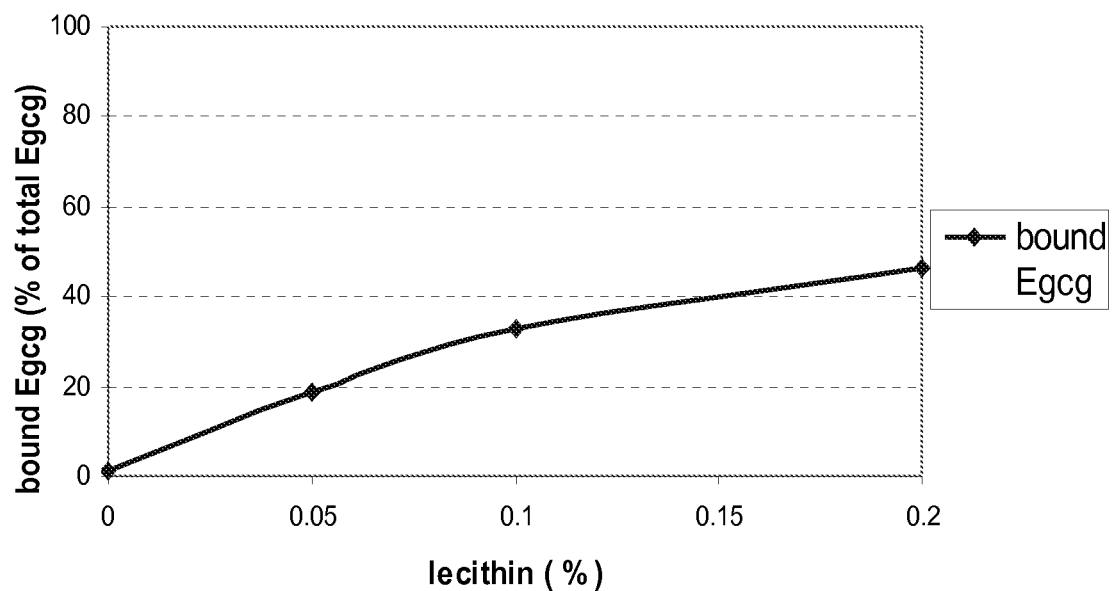

REDUCING ASTRINGENCY IN COMPOSITIONS CONTAINING PHENOLIC COMPOUNDS

The present invention in general relates to the field of taste. In particular it relates to the reduction of astringency. One embodiment of the present invention relates to the use of at least one phospholipid for the preparation of composition containing phenolic compounds to reduce the astringency of the composition.

A phenolic compound is for the purpose of the present invention any compound that contains at least one hydroxyl bound to an aromatic ring.

Phenolic compounds, that are the subject of the present invention, are found in many fruits such as apples, blackberries, cranberries, grapes, peaches, pears, plums, raspberries, and strawberries. Vegetables such as cabbage, celery, onion and parsley also contain a large quantity of phenols. Phenolic compounds are also present in coffee, chocolate, tea and wine. These compounds include monomeric single ring phenolic compounds such as gallic and compounds such as flavanols, flavonols, and anthocyanidins. Oligomeric and polymeric compounds that contain different multiples of the above monomer molecules, and the acylated and/or glycosylated derivatives of many of these groups of compounds are also included.

The well known green tea phenols, the catechins, are flavonoids (flavan-3-ols) that make up as much as 15% of the dry weight of fresh tea leaves. Unfermented green tea contains four main catechins: epicatechin (EC), epicatechin gallate (ECG), epigallocatechin (EGO) and epigallocatechin gallate (EGCG). Epigallocatechin gallate (EGCG) is the most abundant catechin in tea.

Because of their chemical structure, plant phenols are able to scavenge free radicals and inactivate other pro-oxidants. With regard to their antioxidant activity, many health benefits have been attributed to the dietary consumption of natural phenolics (Shahidi, F. and Ho, C. T. (2005) ACS Symp. Ser., 909, 1-8; Scalbert, A., et al., (2005) Crit. Rev. Food Sci. Nutr., 45, 287-306).

Numerous epidemiological studies have addressed the relationships between tea consumption and the incidence of cardiovascular diseases and cancer in humans. Several of these studies have demonstrated significant risk reduction for cardiovascular diseases in consumers of black and green tea. Moreover, there is some evidence that high doses of green tea provides benefit in preventing cancers of the digestive tract, especially gastric cancer (Higdon, J. V. and Frei, B. (2003) Critical Reviews in Food Science and Nutrition 43, 89-143).

Phenols are easily oxidized at neutral to basic pH leading to a rapid loss of these compounds in the presence of oxygen. Decreased stability of phenols under physiological conditions prevailing in the gut has been invoked to explain their low bioavailability (Manach, C., et al., (2005) Review of 97 bioavailability studies, Am. J. Clin. Nutr., 81, 230S-242S).

Phenols are responsible for the astringency of many beverages and foods. Astringency is described as a puckering, rough, or drying mouth-feel and is thought to be caused by the interaction of phenols with basic salivary proline-rich proteins (PRPs). It is widely assumed that the molecular origin of astringency is the precipitation of PRPs following phenol binding and the consequent change to the mucous layer in the mouth. Although only phenols of higher molecular masses can precipitate salivary proteins, flavan-3-ol monomers, flavan-3-ol dimers and trimers, and hydroxybenzoic acids have been shown to elicit the sensation of astringency. Astringency of these smaller phenols may arise from formation of unprecipitated complexes with proteins or cross-linking of proteins with simple phenols that have 1,2-dihydroxy or 1,2,3-trihydroxy groups (Lesschaeve I. and Noble A. G. (2005) American Journal of Clinical Nutrition, 81 (supplement) 330S-335S).

The sensation of astringency is sufficiently unpleasant to some people that it limits the consumer market for associated products. For example, although green tea may provide substantial dietary benefits, many people avoid this beverage because of its astringency. A typical method to cope with the astringency of an ingredient is to increase the sweetness of the whole food.

Unfortunately, increasing the sweetness only partially masks the astringency. In addition, the caloric level can be undesirably increased if the sweetness is raised by increasing a sugar component, such as sucrose or a similar sugar.

Consequently, it was the object of the present invention to provide a method to reduce astringency in astringent beverages and foods while maintaining desirable sensory properties of the product. It would be even more desirable to have a food with reduced astringency and fewer calories than the original product.

The present inventors were surprised to see that they could achieve this object by a use in accordance with claim 1.

Consequently, one embodiment of the present invention is the use of at least one phospholipid for the preparation of a composition containing at least one phenolic compound to reduce the astringency of the composition.

Astringency is a well defined term in the scientific field that is distinct and hence must be separated from bitterness, for example.

Reference is made to the article of Isabelle Lesschaeve and Ann C Noble, published in Am J Clin Nutr 2005; 81 (suppl): 330S-5S, the disclosure of which is hereby incorporated by reference. Astringency is described sensorially as a puckering, rough, or drying mouth-feel, whereas an astringent is defined chemically as a compound that precipitates proteins. For water-soluble phenols, molecular weights between 500 and 3000 were reported to be required. Consistent with this definition, an assay for tannins was developed by Adams and Harbertson (Am J Enol Vitic 1999; 50:247-52).

Astringency is normally perceived, when a composition is brought into contact with the mouth. Consequently, in one embodiment the composition of the present invention is to be brought into contact with the mouth.

This includes but is not limited to products intended for human or animal consumption. For example also cosmetical preparations or creams that are intended for external application might come directly or indirectly into contact with the mouth.

Preferably, the phenol containing composition is selected from the group consisting of foodstuff, medicaments, nutraceuticals, food additives, drinks, pet food, oral cosmetics and dental care products.

Any phospholipid or combination of phospholipids may be used for the purpose of the present invention. In particular acidic, or neutral may be used.

In a particular preferred embodiment of the present invention, the phospholipid is neutral and even more preferably selected from the group consisting of neutral phospholipids, such as phosphatidylcholine, phosphatidylethanolamine and lyso-derivatives thereof, sphingomyelin; acidic phospholipids, such as phosphatidylserine, phosphatidic acid, phosphatidylglycerol, diphosphatidylglycerol, monoacylglycerol monophosphate, monoacylglycerol diphosphate, bisphosphatidyl-monophosphatidic acid, phosphatidylinositol, phosphatidylinositol phosphates, or acidic lysophospholipids, such as lysophosphatidylserine, lysophosphatidic acid, lysophosphatidylinositol, lysophosphatidylglycerol, bisphosphatidyl-lysophosphatidic acid; or mixtures thereof.

In a particular preferred embodiment of the present invention, only neutral phospholipids are used. This has the advantage that these phospholipids allow to create the require structures for reducing astringency in even complex food systems and thus can be applied in a wide range of products.

The phenolic compounds that cause astringency are often present in the form of plants, fruits, animal products, and/or extracts thereof.

Preferably, the phenolic compounds are provided in the form of an extract from a natural food product.

As mentioned above, the phenolic compounds may be found in many fruits such as apples, blackberries, cranberries, grapes, peaches, pears, plums, raspberries, and strawberries; vegetables such as cabbage, celery, onion or parsley.

Also, the composition may comprise citrus fruits, berries, grapes, cocoa, walnuts, peanuts, pomegranates, yerba mate, vegetables, seasoning, flavoring materials, soybean; milk, marine products, nuts, fermented foods, cocoa, coffee, chocolate; tea, in particular black tea, green tea, fermented tea, semi-fermented tea, wine, beer, olive oil, extracts or parts thereof.

Typical phenols that may be used in accordance with the present invention are preferably selected from the group consisting of hydroxybenzoic acids and flavonoid phenols, including flavanols and flavonols, such as the flavan-3-ol monomers, for example, catechin, epicatechin, epigallocatechin, epicatechin gallate, and epigallocatechin gallate and their oligomers and polymers, for example proanthocyanidins or condensed tannins.

Any amount of phospholipids will be effective in reducing the astringency, in particular the perceived astringency, of a product containing phenolic compounds.

The effectiveness of the phospholipids follows essentially a dose-response curve.

However, in a preferred embodiment the composition comprises phospholipids and phenols in a weight ratio in the range of 1:10 to 10:1, preferably in the range 1:2 to 4:1.

In one embodiment of the present invention the phospholipids are used in the phenol containing composition in an amount in the range of 0.01-80 weight parts of the composition, preferably in an amount in the range of 0.05-5 weight parts of the composition.

The present inventors have also found that phospholipids can not only be used to reduce the astringency of a composition that contains phenolic compounds, but alternatively or additionally they may be used to increase the stability of phenols.

Further, alternatively or additionally they may be used to increase the bioavailability of the phenolic compounds and/or to improve the taste of a phenol containing composition.

Those skilled in the art will understand that they can freely combine all features of the present invention described herein, without departing from the scope of the invention as disclosed. In particular, features described for the uses of the present invention may be applied to the foodstuff of the present invention and vice versa.

Further advantages and features of the present invention are apparent from the following Example and FIGURE.

FIG. 1 shows the binding of Egcg in green tea by lecithin.

EXAMPLE

Effect of Phospholipids on Taste and Stability of Catechins

The effect of phospholipids on green tea catechin taste and stability was determined. In addition the formation of a complex was shown between phospholipids and catechins.

Materials

Green tea extract was from Choladi factory, India (batch 52160450; January 2006). Soya lecithin (Phospholipon 80; batch 60351; Phospholipid GmbH) is a product rich in phospholipids containing about 80% of phosphatidylcholin.

Preparation of Green Tea Samples

Soya lecithin was dispersed in distilled water to yield different concentrations (0.05%; 0.1% and 0.2%) by stirring the mixes at 37° C. for 2 h. Phosphate buffer was added to each sample to give a final concentration of 20 mM at pH 6.0 before they were pre-homogenized with an Ultraturrax at full speed. The dispersions were flushed with nitrogen for 5 minutes and then green tea extract was added for a final concentration of 0.2%. After gentle stirring for 15 min the mixes were finally homogenized with a Microfluidizer processor (Microfluidics, Newton, Mass., USA) with 1 run at 250 bar. The same protocol was followed for preparing the green tea control except that no lecithin was added. The homogenized dispersions were filled into 1 lt glass bottles and were sterilized (30 sec at 80° C.) in a water bath heated with steam.

Storage of Green Tea Samples

The sterilized samples were stored at room temperature up to 25 days. No microbiological contamination with mesophilic germs or Enterobacteriaceae was detected throughout the storage test.

Catechin Analysis

Green tea catechins were analysed in the fresh and stored samples by HPLC on a C-18 column, using UV detection at 280 nm. For total catechin determination samples were treated with concentrated acetic acid and the extracts were stabilised with ascorbic acid, EDTA and acetonitrile. For free catechin determination each sample was previously spun at 14,000×g for 30 min using an Eppendorf (Dr Vaudaux A G, Binningen, C H) centrifuge 5415. The resulting supernatant was then treated as previously described. Stability and binding to phospholipids were calculated for (−)-epigallocatechin (Egc), (−)-epigallocatechin-3-gallate (Egcg), and caffeine.

Sensory Evaluation

Panel 21 panellists (internal and external) previously trained for the evaluation of astringency participated in the sensory test.

Test

The intensity of astringency of each green tea sample was scored on a 0-10 linear scale (0=no astringency, 10=strong astringency). At the beginning of the session green tea alone (control) was tasted to illustrate maximal astringency, respectively (score10). The intensity of astringency was assessed for each of the 4 samples having a different lecithin concentration (0 to 0.15%). The samples were presented monadic and in a balanced order. A pause of 3 minutes was respected between each sample where the taster had the possibility to rinse the mouth and neutralize the taste by chewing bread.

Presentation of Samples

The samples were presented under red light in dark coloured Eppendorf tubes of 1.5 mL to mask the differences in appearance due to the dispersed lecithin. Tasters were instructed to put the complete content of the tube in their mouth to evaluate the taste and then spit it. Each sample was presented in duplicate to allow the taster to repeat any tasting when desired.

Results and Discussion

Free and Bound Green Tea Catechins

Green tea samples containing increasing concentrations of lecithin (0.05; 0.1; 0.15%) were analysed for free and bound catechins. Green tea catechins not bearing a gallate moiety showed only a very faint binding to the lecithin. On the contrary green tea catechins with a gallate moiety (Egcg and Ecg) have been found to interact with the added lecithin, yielding fractions of bound and free catechins. The ratio of bound to free catechin gallates increased with the amount of lecithin added to the green tea (see FIG. 1 for the results with Egcg).

Without wishing to be bound by theory, the inventors presently assume that Ecg and Egcg as the "most lipophilic" catechins in green tea have a certain affinity for phospholipids, in particular lecithin, and could reversibly bind to them.

Impact of Lecithin on Green Tea Astringency

The astringency of the lecithin containing green tea samples was determined by sensory evaluation (Table 1).

The statistical analysis of astringency scores attributed to each of the four samples, as well as the relation between lecithin concentration and the reducing effect on astringency show a clear decrease of astringency with the increasing concentration of lecithin. Nevertheless, the ANOVA (Analysis of Variance) shows that the different concentrations of lecithin are not significantly discriminated (p=0.14)

Table 1 shows mean scores, standard deviation and confidence interval for the perceived astringency in green tea in function of the lecithin concentration

|  | Conc. lecithin (%) | | | |
| --- | --- | --- | --- | --- |
|  | 0.00 | 0.05 | 0.10 | 0.15 |
| astringent | 7.27 | 6.33 | 5.52 | 5.71 |
| Std. Dev. | 2.31 | 3.07 | 2.49 | 3.12 |
| Conf. Int. 5% | 1.08 | 1.43 | 1.16 | 1.46 |

The catechins with a gallate moiety (Egcg and Ecg) have been reported to have a much more pronounced effect on astringency than the other green tea catechins (Hayashi, N., et al, (2005) Biosc. Biotechnol. Biochem., 69, 1306-1310). The presently reported binding of Egcg and Ecg with phospholipids should limit a possible interaction of these catechins with saliva proteins and with corresponding receptors in the mouth. This could thus explain why a reduced astringency was found for samples containing a phospholipid, in particular lecithin.

Impact of Lecithin on Green Tea Stability

The same green tea samples used for the tasting of astringency were analysed for their stability during storage.

The protection by phospholipids of catechin gallates against oxidative decomposition (Table 2) can also be explained based on the interaction of these green tea catechins with phospholipids, in particular, if the interactions persist during shelf life.

TABLE 2

Stability of Egc and total Egcg during storage

| green tea 0.2% catechins (% recovered) | | | green tea 0.2% + lecithin 0.05% catechins (% recovered) | | |
| --- | --- | --- | --- | --- | --- |
| storage(d) | Egc | Egcg | storage(d) | Egc | Egcg |
| 0 | 100 | 100 | 0 | 100 | 100 |
| 2 | 93 | 94 | 2 | 92 | 95 |
| 9 | 65 | 67 | 9 | 72 | 78 |
| 13 | 50 | 53 | 13 | 59 | 68 |
| 22 | 28 | 33 | 22 | 42 | 55 |

| green tea 0.2% + lecithin 0.1% catechins (% recovered) | | | green tea 0.2% + lecithin 0.2% catechins (% recovered) | | |
| --- | --- | --- | --- | --- | --- |
| storage(d) | Egc | Egcg | storage(d) | Egc | Egcg |
| 0 | 100 | 100 | 0 | 100 | 100 |
| 2 | 94 | 98 | 2 | 91 | 99 |
| 9 | 70 | 82 | 9 | 64 | 88 |
| 13 | 57 | 74 | 13 | 49 | 82 |
| 22 | 39 | 62 | 22 | 30 | 71 |

Indeed, the analysis of free and bound catechins in phospholipid—for example lecithin—containing green tea samples during storage revealed that the percentage of bound Egcg not only remained constant but rather slightly increased with time (Table 3). This increase is due to the changing ratio between free and bound Egcg caused by the preferential degradation of the free form.

TABLE 3

Interaction between Egcg and lecithin during storage

| green tea 0.2% bound catechins (% recovered in pellet) | | | green tea 0.2% + lecithin 0.05% bound catechins (% recovered in pellet) | | |
| --- | --- | --- | --- | --- | --- |
| storage(d) | Egc | Egcg | storage(d) | Egc | Egcg |
| 0 | 3 | 1 | 0 | 1 | 18 |
| 2 | 0 | 1 | 2 | 3 | 17 |
| 9 | 0 | 1 | 9 | 1 | 21 |
| 13 | 0 | 2 | 13 | 1 | 22 |
| 22 | 0 | 2 | 22 | 0 | 22 |

| green tea 0.2% + lecithin 0.1% bound catechins (% recovered in pellet) | | | green tea 0.2% + lecithin 0.2% bound catechins (% recovered in pellet) | | |
| --- | --- | --- | --- | --- | --- |
| storage(d) | Egc | Egcg | storage(d) | Egc | Egcg |
| 0 | 2 | 33 | 0 | 5 | 46 |
| 2 | 4 | 30 | 2 | 6 | 45 |
| 9 | 2 | 37 | 9 | 5 | 53 |
| 13 | 2 | 38 | 13 | 5 | 55 |
| 22 | 2 | 39 | 22 | 6 | 59 |

The dose-dependent stabilisation of Egcg by lecithin during storage of the green tea samples (Table 3) may well support the hypotheses that the catechin is protected through interaction with the phospholipids. Among the other green tea constituents, the xanthine alkaloide caffeine was found to be quite stable under the chosen storage conditions, independently of any interaction with lecithin.

Taking into account these results, we may conclude that the same mechanism, i.e. binding of gallate catechins to lecithin vesicle interfaces, could be responsible for the protection of these catechins during storage as well as for the reduced astringency perceived during tasting of such green tea preparations.

The invention claimed is:

1. A method for reducing the astringency of a composition that comprises a catechin, the method comprising the step of adding a phosphatidylcholine to the composition, the phosphatidylcholine and the catechin are in a weight ratio from 1:2 to 4:1.

2. The method of claim 1, wherein the composition is designed to be brought into contact with the mouth.

3. The method of claim 1, wherein the composition is selected from the group consisting of foodstuff, medicaments, nutraceutical, food additives, drinks, pet food, oral cosmetics and dental care products.

4. The method of claim 1, wherein the composition comprises a component selected from the group consisting of citrus fruits, berries, grapes, cocoa, walnuts, peanuts, pomegranates, yerba mate, vegetables, seasoning, flavoring materials, soybean, milk, marine products, nuts, fermented foods, cocoa, coffee, chocolate, tea, wine, beer, olive oil, extracts and parts thereof.

5. The method of claim 1, wherein the catechin is provided in a form of an extract from a natural food product.

6. The method of claim 1, wherein the weight ratio of the phosphatidylcholine and the catechin is 1:1.

7. The method of claim 1, wherein only neutral phosphatidylcholine is used.

8. The method of claim 1, wherein the phosphatidylcholine is used in the composition in an amount of 0.01-80 wt % of the composition.

\* \* \* \* \*